United States Patent [19]

Howell et al.

[11] Patent Number: 5,128,263
[45] Date of Patent: Jul. 7, 1992

[54] ENZYMATIC RESOLUTION PROCESS HYDROLYZING THIO-ESTER

[75] Inventors: Jeffrey M. Howell, Chatham; Ramesh N. Patel, Bridgewater; Laszlo J. Szarka, East Brunswick, all of N.J.

[73] Assignee: E. R. Squibb & Sons, Inc., Princeton, N.J.

[21] Appl. No.: 427,078

[22] Filed: Oct. 25, 1989

Related U.S. Application Data

[63] Continuation-in-part of Ser. No. 219,624, Jul. 14, 1988, abandoned.

[51] Int. Cl.$^5$ .............................................. C12P 7/62
[52] U.S. Cl. ..................................... 435/280; 435/135
[58] Field of Search ................................ 435/280, 135

[56] References Cited

U.S. PATENT DOCUMENTS 4,629,701 12/1986 Sakimae et al. .

FOREIGN PATENT DOCUMENTS 8700517 9/1987 PCT Int'l Appl. .

*Primary Examiner*—Sam Rosen
*Attorney, Agent, or Firm*—Thoedore R. Furman, Jr.

[57] ABSTRACT

A novel enzymatic resolution process for preparing resolved compounds of the formula

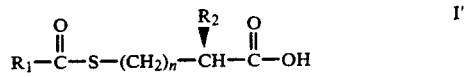

$$R_1-\overset{O}{\underset{\|}{C}}-S-(CH_2)_n-\overset{R_2}{\underset{}{C}}H-\overset{O}{\underset{\|}{C}}-OH \qquad I'$$

with improved yields and high optical purity is disclosed. The thioester bond of the compound is hydrolyzed and the hydrolyzed compound is separated from the unhydrolyzed. Compounds of formula I' are useful, for example, as intermediates for the preparation of physiologically active compounds, e.g. captopril and zofenopril.

11 Claims, No Drawings

ENZYMATIC RESOLUTION PROCESS HYDROLYZING THIO-ESTER

This is a continuation-in-part of U.S. Ser. No. 219,624 filed Jul. 14, 1988, now abandoned.

BACKGROUND OF THE INVENTION

Optically active carboxylic acids represented by the formula

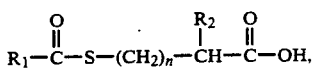

wherein $R_1$ and $R_2$ are each independently selected from alkyl, cycloalkyl, aralkyl or aryl, and n is 1 or 2, are useful, for example, as intermediates for the synthesis of various physiologically active materials. For example, a compound of the formula

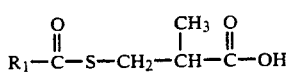

is a key intermediate in the synthesis of 1-(2S)3-mercapto-2-methylpropionyl]-L-proline (captopril), having the formula

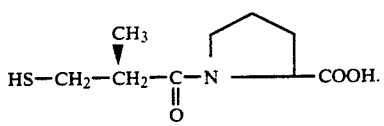

The beneficial activity of captopril depends on the configuration of the mercapto-alkanoyl moiety and the compound of the S configuration is about 100 times more potent than the corresponding R-enantiomer.

Prior art processes for making captopril have utilized chemical and enzymatic resolution procedures. For example, carboxylic acids of formula I are prepared as racemic mixtures which can be separated into the R and S-enantiomeric forms using chemical resolving agents. The so-provided S intermediates can then be used to prepare the desired product. The chemical resolution techniques have the distinct disadvantage, however, that large amounts of very expensive resolving agents are required to make captopril. Additionally, the processes themselves are cumbersome and the yield is relatively low.

Alternatively, racemic compounds of the formula

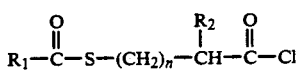

can be directly coupled to L-proline to produce diastereomers of the general formula

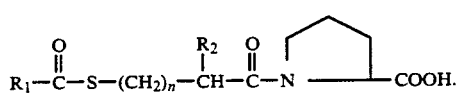

The SS-diastereomer of compound V can be isolated. Subsequent removal of the

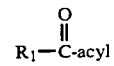

group provides the desired product. However, a drawback to this process is that an equal amount of the RS-diastereomer of compound V is formed which must be discarded. This is highly undesirable in view of the cost of the L-proline.

U.S. Pat. No. 4,629,701 provides the desired resolved form of the carboxylic acids of formula I by subjecting an ester of the formula

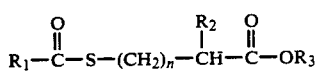

to an enzyme capable of asymmetrically hydrolyzing such an ester. It was found that while the

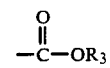

moiety is hydrolyzed to the acid form, the racemic ester is also resolved into the S or R configuration in improved yields and at lower costs than possible with chemical resolution techniques. However, there is still a considerable expense in making these ester starting materials and higher optical purity is still desired for more active products. Therefore, a process which is less expensive with improved yields and which provides enhanced optical purity would be a useful addition to the art.

SUMMARY OF THE INVENTION

In accordance with the present invention, a novel process for preparing S-enantiomers of the formula

wherein $R_1$ and $R_2$ are each independently selected from alkyl, cycloalkyl, aralkyl or aryl, and n is 1 or 2, is provided. The process comprises treating a racemic mixture of a compound of formula I with an enzyme or microorganism having the ability to asymmetrically hydrolyze the thioester bond of I, in the presence of a solvent.

DETAILED DESCRIPTION OF THE INVENTION

The following definitions apply throughout this application.

The term "alkyl" as used herein refers to straight or branched chain carbon groups of 1 to 20 carbon atoms, preferably 1 to 6 carbon atoms.

The term "cycloalkyl" as used herein refers to groups containing 5 to 7 carbon atoms.

The term "aryl" as used herein refers to monocyclic or bicyclic aromatic groups containing from 6 to 10 carbon atoms in the ring portion such as phenyl, naphthyl, and substituted phenyl or naphthyl containing substituents such as nitro, halogen, methyl or alkoxy groups on the aromatic ring.

The enzymatic resolution process of the present invention has the advantage that it can provide the desired S-enantiomers of formula I' with optical purity of 95 percent and above at yields exceeding 20 percent. Additionally, because the present process uses a racemic carboxylic acid of formula I as a starting material, instead of the carboxylic acid esters employed in prior art enzymatic processes, there is considerably less expense involved. These and other features make the process of the present invention very attractive for use in preparing optically active compounds of formula I', such as the S-enantiomer of the formula

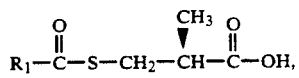  II' useful in the preparation of captopril.

As discussed above, the prior art enzymatic processes function by the hydrolysis of the carboxy-ester, i.e. hydrolysis of the

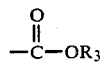

moiety in formula VI above to a

group.

In the present process, the racemic form of a compound of formula I is the starting material. Since this material does not include a carboxy ester, the enzyme or microorganism employed selectively catalyzes the hydrolysis of the thioester bond of one enantiomer of racemic I to yield the resolved form of the compounds of formula I' with high optical purity.

Methods for obtaining the racemic starting material of the formula

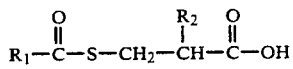  I are known.

For example, a compound of the formula

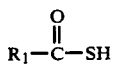  VII can be coupled to a compound of the formula

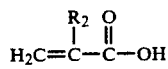  VIII in the presence or absence of a suitable solvent, such as hexane, heptane or isopropanol, under the usual conditions for conducting such an addition reaction.

The present process can be carried out in an aqueous solvent, or organic solvent or mixtures thereof. Typical solvents suitable for use in the present process include, but are not limited to, 1,1,2-trichloro-1,2,2-trifluoroethane, toluene, cyclohexane, benzene, deionized water, suitable aqueous buffer solutions and mixtures of these organic and aqueous solvents.

The enzyme or microorganism used in the present process can be any enzyme or microorganism having the ability to asymmetrically hydrolyze thioesters of the general formula I. Various enzymes, such as esterases, lipases and proteases regardless of origin or purity, are suitable for use in the present invention. The enzyme can be in the form of a mixture of animal and plant enzyme, cells of microorganisms, crushed cells or extracts of cells.

Typical genuses of microorganism suitable as sources of hydrolyzing enzymes include Mucor, Escherichia, Staphylococcus, Agrobacterium, Rhizopus, Aspergillus, Nocardia, Streptomyces, Trichoderma, Candida, Rhodotorula, Torulopsis, Bacillus, Alcaligenes, Pseudomonas, Brevebacterium, Enterobacter, Chromobacterium, Arthrobacter, Microbacterium, Mycobacterium, Saccharomyces, Penicillium, Botrytis, Chaetomium, Ophiobolus, Cladosporium and the like.

Commercially available enzymes suitable for use in the present invention include lipases, such as Amano AY-30 (*Candida cylindracea*), Amano P (*Pseudomonas fluorescens*), Amano N (*Rhizopus niveus*), Amano R (*Penicillium sp.*), Amano FAP (*Rhizopus oryzae*), Amano AP-12 (*Aspergillus niger*), Amano MAP (*Mucor meihei*), Amano GC-4 (*Geotrichum cadidum*), Sigma L-0382 (porcine pancreas), Sigma L-3001 (Wheat germ), Sigma L-1754 (*Candida cylindracea*), Sigma L-0763 (*Chromobacterium viscosum*) and Amano K-30 (*Aspergillus niger*). Additionally, enzymes derived from animal tissue include esterase from pig liver, α-chymotrypsin and pancreatin from pancreas.

Specific microorganisms suitable for use in the present process include *Pseudomonas fluorescens, Pseudomonas putida, Pseudomonas ovalis, Escherichia coli, Staphylococcus aureus, Alcaligenes faecalis, Streptomyces griseus, Streptomyces clavuligerus, Nocardia erthropolis, Nocardia asteraides, Mycobacterium phle, Agrobacterium radiobacter, Aspergillus niger, Rhizopus oryzae* and the like.

To carry out the process of the present invention, the enzyme and racemic starting material are added to the desired solvent. Typically, the enzyme is adsorbed onto a suitable carrier, e.g. diatomaceous earth (porous Celite Hyflo Supercel), or the like. This serves the purpose of immobilizing the enzyme which has the effects of controlling the enzyme particle size and preventing aggregation of the enzyme particles when used in an organic solvent. This can be accomplished, for example, by precipitating an aqueous solution of the enzyme with cold acetone in the presence of the Celite Hyflo Supercel followed by vacuum drying. The reaction solution typically contains between about 5 and 200 mg of racemic starting material per ml of solvent, and preferably contains about 15–50 mg/ml. The enzyme added to the reaction solution may be present in concentrations ranging from about 5 to about 40 mg of enzyme per ml of solvent. While it is desirable to use the least amount of enzyme possible, the amount of enzyme required will vary depending upon the specific activity of the enzyme used.

When the reaction is conducted in an organic solvent, small amounts of water may be added to the reaction mixture. The water added to the reaction mixture may be present in concentrations ranging from about 0.2 to about 100 mg of water per ml of solvent, or solvent saturated with water, and preferably is present in an amount of about 0.8–5 mg/ml. When an aqueous buffer solution or deionized water is used as the solvent for the reaction, the pH of the reaction solution may be between about 3 and 10, and is preferably maintained at about 5–8 by the addition of suitable materials. Incubation of the reaction solution can be at a temperature between about 4 and about 60° C. and is preferably carried out at about 30° C. The reaction time can be appropriately varied depending upon the amount of enzyme used and its specific activity. Typical reaction times for optical purities of 90 percent and above are at least about 5 hours and can range up to about 50 hours for greater conversions and higher optical purities, e.g. optical purities exceeding 95 percent. Optically active I' can be isolated from the reaction mixture and purified by known methodologies such as extraction, distillation, crystallization, column chromatography, and the like.

As will be apparent to those skilled in the art, the process of the present invention can be carried out using microbial cells containing an enzyme having the ability to asymmetrically hydrolyze thioesters of the general formula I. When using a microorganism to perform the resolution, the present process is conveniently carried out by adding the cells and the racemic starting material to the desired solvent. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract.

Using the methodology of U.S. Pat. No. 4,105,776, the resolved acid of formula I' or its chemical equivalent is used to acylate L-proline having the formula

forming captopril, i.e. the compound of formula III. The thioester formed by the coupling of compound I with compound IX can be deacylated by conventional means, such as by ammonolysis (e.g., by treatment with alcoholic ammonia or concentrated ammonium hydroxide) or by alkaline hydrolysis (e.g., by treatment with aqueous metal hydroxide). Alternatively, again employing methodology from U.S. Pat. No. 4,105,776, the resolved acid of formula I' can be used by removing the acetyl group (by conventional methods) and thereafter dehydrating the so-treated acid to form a thiolactone of the formula

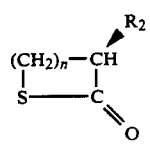

The thiolactone X can thereafter be used to acylate the L-proline of formula IX to obtain the desired product.

Similarly, to provide zofenopril, i.e., the compound of the formula

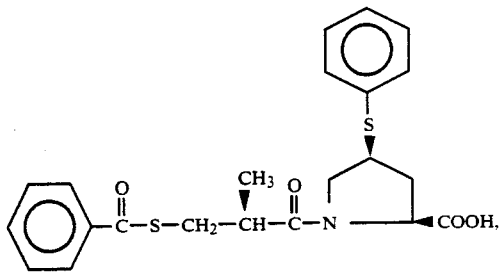

the resolved acid of formula I' or its chemical equivalent where $R_1$ is

is used to acylate a compound of the formula

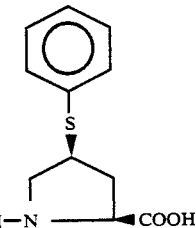

as described in U.S. Pat. No. 4,316,906. Alternatively, using the methodology of U.S. Pat. No. 4,316,906, the compound of formula I' where $R_1$ is

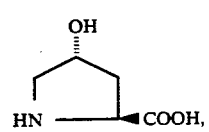

can be coupled with a compound of the formula

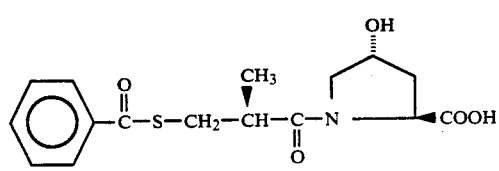

or esters or protected forms thereof, to provide a compound of the formula

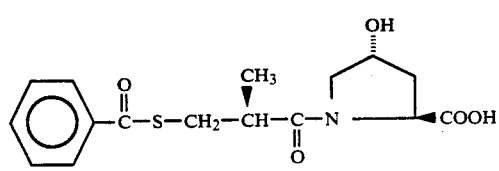

which can thereafter be treated with a compound of the formula

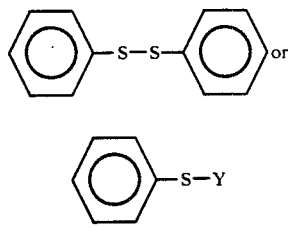

where Y is an activating group such as succinimide or phthalamido or a halide such as Cl or Br to provide the product of formula XI.

The acylation of compounds IX, XII or XIII with the resolved acid of formula I' can be effected in the presence of a coupling agent like dicyclohexycarbodiimide or the like, or the acid can be activated by formation of its mixed anhydride, symmetrical anhydride, acid chloride, acid ester or use of Woodward reagent K, N-ethoxy-carbonyl-2-ethoxy-1,2-dihydroquinoline or the like. For a review of the methods for acylation, see *Methoden der Organischen Chemie* (Houben-Weyl), Vol. XV, part II, page 1 et seq. (1974).

The present invention will now be described by the following examples, however, it should be understood that the invention is not meant to be limited by the details therein.

EXAMPLE 1

To a solution of racemic 3-acetylthio-2-methylpropanoic acid (405 mg) in 25 ml of 1,1,2-trichloro-1,2,2-trifluoroethane (CFC-113) was added 1.0 g of lipase from *Pseudomonas fluorescens (Amano lipase P*-30) and 90 mg of deionized water. The reaction mixture was shaken on a gyrotary shaker at 280 rpm at 30° C. The degree of conversion was followed by gas chromatography of reaction mixture filtrates. After 16 hours, the conversion was 84% based on the racemic material initially present. The enantiomeric composition of the remaining unreacted substrate (obtained in 16% reaction yield) was 97.8% S-enantiomer and 2.2% R-enantiomer of 3-acetylthio-2-methylpropanoic acid (enantiomeric excess =95.6%). In this and all following examples, the enantiomeric composition of the unreacted 3-acetylthio-2-methylpropanoic acid fraction was determined by capillary gas chromatography following derivatization with thionyl chloride and esterification of the resulting acid chloride with (S)-(+)-2-octanol to form diastereomeric esters which can be separated by capillary GC.

EXAMPLE 2

10.0 g of lipase from *Pseudomonas fluorescens* (Amano lipase P-30) was added to 50 ml deionized water and the mixture centrifuged for 10 minutes at 1,000×G. A 40 ml portion of the supernatant was diluted to 200 ml with deionized water and to this enzyme solution was added 4.0 g of Celite Hyflo Supercel (diatomaceous ear&:h supplied by Manville Corporation). The mixture was incubated for 3 hours at 28° C. with gentle stirring The enzyme was then precipitated onto the Hyflo Supercel by slowly adding 300 ml of ice-cold acetone to the mixture while stirring. The mixture was filtered on a sintered glass vacuum filter and the filter cake washed with 300 ml ice-cold acetone. The preparation was dried in a vacuum evaporator at 50° C. for 18 hours to yield an immobilized enzyme preparation with a water content of 0.45% w/w (Karl Fischer moisture analysis).

A 2 g portion of the above immobilized enzyme preparation was added to a solution of racemic 3-acetylthio-2-methylpropanoic acid (405 mg) in 25 ml of 1,1,2-trichloro-1,2,2-trifluorethane (CFC-113). To this mixture, 60 mg of deionized water was added and the reaction mixture shaken on a gyrotary shaker at 280 rpm at 30° C. The degree of conversion was followed by high-pressure liquid chromatography (HPLC) of reaction mixture filtrates. After 12 hours, the conversion was 78% based on the racemic substrate initially present. The enantiomeric composition of the remaining unreacted substrate (obtained in 22% reaction yield) was 97.1% S-enantiomer and 2.9% R-enantiomer of 3-acetylthio-2-methylpropanoic acid (enantiomeric excess =94.2%) as determined by capillary gas chromatography following derivatization.

EXAMPLE 3

A 2 g portion of the immobilized enzyme preparation described in Example 2 was added to a solution of racemic 3-acetylthio-2-methylpropanoic acid (405 mg) in 25 ml of toluene. To this mixture, 60 mg of deionized water was added and the reaction mixture shaken on a gyrotary shaker at 280 rpm at 28° C. After 28 hours, the conversion was 79% complete (HPLC analysis) based on the racemic substrate initially present. The enantiomeric composition of the remaining unreacted substrate (obtained in 21% reaction yield) was 97.5% S-enantiomer and 2.5% R-enantiomer of 3-acetylthio-2-methylpropanoic acid (enantiomeric excess =95.0%).

EXAMPLE 4

405 mg of racemic 3-acetylthio-2-methylpropanoic acid was dissolved in 15 ml of deionized water, the pH adjusted to 5.0 with 1 N sodium hydroxide, and the solution diluted to 25 ml with deionized water. This solution was placed in a magnetically stirred pH-stat vessel at 40° C. with pH maintained at 5.0 by the addition of 0.5 N sodium hydroxide. To this solution was added 1.0 g of lipase from *Pseudomonas fluorescens* (Amano lipase P-30) and the degree of conversion followed by HPLC analysis. After 40 hours, the conversion was 76% based on the racemic substrate initially present. The enantiomeric composition of the remaining unreacted substrate (obtained in 24% reaction yield) was 85.7% S-enantiomer and 14.3% R-enantiomer of 3-acetylthio-2-methylpropanoic acid (enantiomeric excess =71.4%) as determined by capillary gas chromatography following derivatization.

EXAMPLE 5

To a solution of racemic 3-acetylthio-2-methylpropanoic acid (405 mg) in 25 ml of 1,1,2-trichloro-1,2,2-trifluoroethane (CFC-113) was added 1.05 g of dried mycelia of *Rhizopus oryzae* (ATCC 24563) and 75 mg of deionized water. The reaction mixture was shaken on a gyrotary shaker at 280 rpm at 28° C. After 69 hours, the conversion was 73% complete (HPLC analysis) based on the racemic substrate initially present. The enantiomeric composition of the remaining unreacted substrate (obtained in 27% reaction yield) was 95.9% S-enantiomer and 4.1% R-enantiomer of 3-acetylthio-2-methylpropanoic acid (enantiomeric excess =91.8%).

What is claimed is:

1. A process for the selective preparation of a specific enantiomer of a compound of the formula

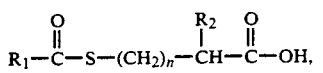

wherein $R_1$ and $R_2$ are each independently selected from alkyl, cycloalkyl, aralkyl and aryl, and n is 1 or 2; which process comprises treating a racemic mixture of a compound of formula I with an enzyme, or microorganism containing an enzyme, capable of asymmetrically hydrolyzing the thioester bond of said compound of formula I in the presence of a solvent and separating the thioester hydrolyzed compound from the unhydrolyzed compound.

2. The process of claim 1 wherein the enzyme is selected from lipase, esterase, α-chymotrypsin and pancreatin.

3. The process of claim 1 wherein the microorganism is selected from *Pseudomonas fluorescens, Pseudomonas putida, Pseudomonas ovalis, Escherichia coli, Staphylococcus aureus, Alcaligenes faecalis, Streptomyces griseus, Streptomyces clavuligerus, Nocardia erthropolis, Nocardia asteraides, Mycobacterium phlei, Agrobacterium radiobacter, Aspergillus niger, Rhizopus oryzae* and the like.

4. The process of claim 1 wherein the solvent is selected from aqueous solvents, organic solvents and mixtures thereof.

5. A process for the preparation for the S-enantiomer having the formula

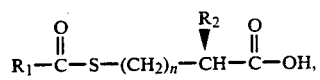

wherein $R_1$ and $R_2$ are each independently selected from alkyl, cycloalkyl, aralkyl and aryl, and n is 1 or 2; which process comprises treating a racemic mixture of a compound of the formula

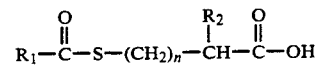

with an enzyme, or microorganism which contains an enzyme, capable of asymmetrically hydrolyzing the thioester bond of said compound of formula I, in the presence of a solvent and separating the thioester hydrolyzed compound from the unhydrolyzed compound.

6. The process of claim 5 wherein the enzyme is selected from lipase, esterase, α-chymotrypsin and pancreatin.

7. The process of claim 5 wherein the microorganism is selected from *Pseudomonas fluorescens, Pseusomonas putida, Pseudomonas ovalis, Escherichia coli, Staphylococcus aureus, Alcaligenes faecalis, Streptomyces griseus, Streptomyces clavuligerus, Nocardia erthropolis, Nocardia asteraides, Mycobacterium phlei, Agrobacterium radiobacter, Aspergillus niger, Rhizopus oryzae* and the like.

8. The process of claim 5 wherein the solvent is selected from aqueous solvents, organic solvents and mixtures thereof.

9. A process for the preparation of a compound of the formula

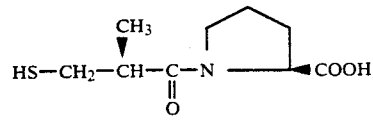

which comprises coupling a resolved carboxylic acid of the formula

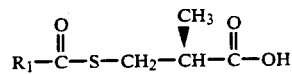

with a compound of the formula

or its chemical equivalent, and thereafter removing the

moiety to provide the desired product; which process is further characterized in that said resolved carboxylic acid is prepared by the process of claim 1.

10. A process for the preparation of a compound of the formula

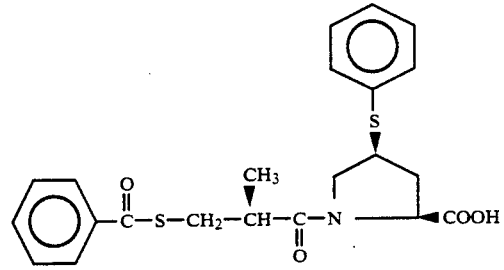

which comprises coupling a resolved carboxylic acid of the formula

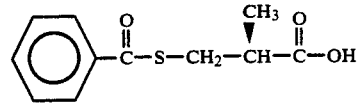

with a compound of the formula

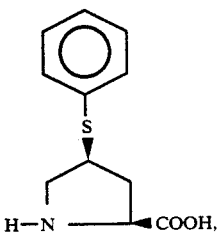

or its chemical equivalent, which process is further characterized in that said resolved carboxylic acid is prepared by the process of claim 1.

11. A process for the preparation of a compound of the formula

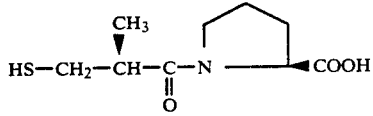

which comprises removing the acetyl group from a resolved carboxylic acid of the formula

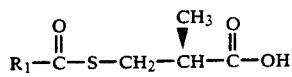

and dehydrating the so-treated acid to form a thiolactone of the formula

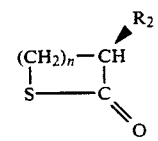

and thereafter acylating a compound of the formula

with said thiolactone to provide the desired product, which product is further characterized in that said resolved carboxylic acid is prepared by the process of claim 1.

* * * * *